United States Patent [19]

Anderson et al.

[11] Patent Number: 5,338,361
[45] Date of Patent: Aug. 16, 1994

[54] MULTIPLE COAT MEASUREMENT AND CONTROL APPARATUS AND METHOD

[75] Inventors: Leonard M. Anderson, San Jose; John J. Howarth, Scotts Valley, both of Calif.

[73] Assignee: Measurex Corporation, Cupertino, Calif.

[21] Appl. No.: 787,071

[22] Filed: Nov. 4, 1991

[51] Int. Cl.$^5$ .............................................. B05C 11/00
[52] U.S. Cl. .................................... 118/689; 118/688; 118/419; 118/413
[58] Field of Search .................. 162/263, 198, 135; 118/665, 419, 429, 689, 688, 413; 250/339, 341, 221; 356/381, 382, 320, 429

[56] References Cited

U.S. PATENT DOCUMENTS

| | | |
|---|---|---|
| 3,228,282 | 1/1966 | Barker, Jr. . |
| 3,405,268 | 10/1968 | Brunton . |
| 3,455,637 | 7/1969 | Howard . |
| 3,476,482 | 11/1969 | Howard et al. . |
| 3,525,863 | 8/1970 | Constantine et al. . |
| 3,614,450 | 10/1971 | Hill et al. . |
| 3,641,349 | 2/1972 | Dahlin . |
| 3,662,170 | 5/1972 | Keyes, IV . |
| 3,675,019 | 7/1972 | Hill et al. . |
| 3,793,524 | 2/1974 | Howarth ............................ 250/339 |
| 3,801,349 | 4/1974 | Wilson .................................. 427/10 |
| 3,827,808 | 8/1974 | Cho . |
| 3,851,175 | 11/1974 | Dahlin et al. . |
| 3,879,607 | 4/1975 | Bjorklund . |
| 3,965,356 | 6/1976 | Howarth . |
| 3,994,602 | 11/1976 | Howarth . |
| 4,006,358 | 2/1977 | Howarth ............................ 162/263 |
| 4,098,641 | 7/1978 | Casey et al. . |
| 4,135,006 | 1/1979 | Readal et al. ........................ 118/665 |
| 4,243,882 | 1/1981 | Yasujima et al. . |
| 4,277,177 | 7/1981 | Larsen et al. . |
| 4,306,151 | 12/1981 | Chase . |
| 4,319,847 | 3/1982 | Howarth . |
| 4,345,150 | 8/1982 | Tamura et al. . |
| 4,577,104 | 3/1986 | Sturm . |
| 4,674,325 | 6/1987 | Kiyobe et al. . |
| 4,743,775 | 5/1988 | Edgar . |
| 4,766,315 | 8/1988 | Hellstrom et al. . |
| 4,769,544 | 9/1988 | Dahlquist . |
| 4,789,820 | 12/1988 | Parrent, Jr. et al. . |
| 4,823,008 | 4/1989 | Sturm . |
| 4,840,706 | 6/1989 | Campbell . |
| 4,928,013 | 5/1990 | Howarth et al. . |
| 4,957,770 | 9/1990 | Howarth ............................ 118/665 |
| 5,124,552 | 6/1992 | Anderson . |

FOREIGN PATENT DOCUMENTS

| | | |
|---|---|---|
| 1196512 | 11/1985 | Canada . |
| 0137696 | 4/1985 | European Pat. Off. . |
| 0279743 | 8/1988 | European Pat. Off. . |
| 2128273 | 6/1971 | Fed. Rep. of Germany . |
| 2318032 | 10/1973 | Fed. Rep. of Germany . |
| 2845995 | 4/1979 | Fed. Rep. of Germany . |
| 53-39194 | 10/1978 | Japan . |
| 59-120940 | 7/1984 | Japan . |
| 61-53549 | 3/1986 | Japan . |
| 61-120004 | 6/1986 | Japan . |
| 1182353 | 9/1985 | U.S.S.R. . |
| 1102062 | 2/1968 | United Kingdom . |
| 2044443 | 10/1980 | United Kingdom . |
| 2127871 | 4/1984 | United Kingdom . |

OTHER PUBLICATIONS

Wesley Wm. Wendlandt and Harry G. Hecht, *Reflectance Spectroscopy* (1966).
K. Takami and C. Shinbo, *Thickness measurement method for thin photoresist film on transparent material*, Rev. Sci. Instrum. 54(6), Jun. 1983.
Vakulyuk et al., *Infrared Water-content Meter for Paper*, Measurement Techniques, vol. 19, No. 7, pp. 1065–1066, Jul., 1976.
Pugh, *The Infrared Measurement of Surface Moisture in Paper*, Tappi, vol. 63, No. 10, pp. 131–134, Oct. 1980.

*Primary Examiner*—W. Gary Jones
*Assistant Examiner*—Brenda Lamb
*Attorney, Agent, or Firm*—Spensley Horn Jubas & Lubitz

[57] ABSTRACT

The present invention relates to apparatuses and methods for measuring and controlling the amount of multiple coating materials applied to a substrate, and in particular to an apparatus and method for monitoring and regulating the amount of multiple coating materials containing different compositions applied to a substrate, such as paperboard. The coating measurement is insensitive to changes in both the amount of substrate as well as in the amount of an interfering component associated with the substrate.

24 Claims, 4 Drawing Sheets

MULTIPLE COAT MEASUREMENT AND CONTROL APPARATUS AND METHOD

BACKGROUND OF THE INVENTION

The present invention relates to apparatuses and methods for measuring and controlling the amount of multiple coating materials applied to a substrate, and in particular to an apparatus and method for monitoring and regulating the basis weight of multiple coating materials containing different compositions applied to a paper sheet, such as paperboard.

It is often desirable to coat paperboard with different types of coating materials to make a white printable surface. Although the paperboard can be coated with a wide variety of materials, it is often first coated with a base coat, which may be composed of a paint-like substance of principally calcium carbonate ($CaCO_3$), a latex binder and possibly some clay. A top coat is then applied which may be composed of principally clay, a latex binder and possibly some $CaCO_3$. Both the $CaCO_3$ and clay serve as white pigments. $CaCO_3$ is the less expensive pigment, but does not enhance the printability of the paperboard as well as clay. Therefore, $CaCO_3$ is preferred as the principal component of the base coat and clay is preferred as the principal component of the top coat on which the printing takes place. The coatings provide a white surface for packaging boxes, such as cereal boxes, shoe boxes, and the like. Alternatively, or in addition, such coatings also may be intended to render paperboard waterproof.

These coatings may be applied to the paperboard as part of the papermaking process in a paper mill. Alternatively, previously manufactured paperboard may be supplied from large rolls of paperboard to separate coating machines, called "coaters." In either process, the uncoated paperboard is usually fed sequentially to the coaters in sheets that are 15 feet or more in their "cross-directional" width (i.e., the direction transverse to the direction of movement of the paper-through the paperboard machinery).

It is often desirable to apply a uniform "basis weight" (i.e., mass of the coating material on a unit of surface area of the sheet) of coating to the substrate. For example, the printability of paperboard is improved by a uniform layer of gloss coating which may include relatively expensive materials, such as latex and/or $TiO_2$. Of course, a uniform coating layer avoids wasting such materials. In some processes, the uniformity of the coatings should be controlled to a fraction of a gram/$m^2$.

Various complex coatere have been designed to handle the relatively large cross-directional width of paperboard and the requirement for a uniform coating. One type of coater, a blade coater, includes a rotating backing drum located adjacent to one side of a moving sheet and a flexible blade located adjacent to the opposite side of the sheet. The drum and blade edge form a narrow slot through which the sheet passes and retain a pool of coating material which coats the sheet as it passes through the slot. The blade edge presses the sheet passing through the slot to remove excess coating.

The distance from the drum to the blade edge is a critical factor; thus, the drum must be fabricated and installed to high tolerances. To control the thickness of the coating applied to a sheet, coaters provide actuators for adjusting the pressure of the blade edge against the coated sheet and/or the position of the blade edge relative to the drum. The blade is usually made of a thin steel member which may be slightly bent or flexed. Actuators are installed at intervals along the length of the blade so that each actuator controls the pressure applied by the blade in the vicinity of the actuator, and therefore, controls the amount of coating applied to the sheet. The cross-directional length of the blade in the vicinity of each actuator is referred to as a "slice." U.S. Re No. 33,741, formerly U.S. Pat. No. 4,732,776 to Boissevain, assigned to Measurex Corporation, describes a coater including this type of coating blade actuator. This reissue patent is incorporated herein by reference.

Local variations in sheet temperature and thickness, and possibly other factors, if not compensated for, will tend to produce uneven coatings. Therefore, it is important to have the ability to measure the amount of coating at various locations on the sheet and to control the pressure of the blade against the sheet at a plurality of cross-directional positions based on the measurements.

U.S. Pat. No. 4,957,770 to Howarth, assigned to Measurex Corporation, describes a coating sensor for measuring the basis weight of a coating on paper by detecting the amount of a single coating component. This patent is incorporated herein by reference. However, applicants are unaware of any apparatus and method, other than their own, which uses a single sensor to measure the amount of multiple coating components to determine the amount of multiple coatings on a substrate. One of the most difficult aspects of multiple coating control is obtaining an accurate measurement of the amount of each of the coating layers applied to a sheet, particularly if the coating must be measured to an accuracy in fractions of a gram/$m^2$.

However, there is a scheme for measuring the amount of two coatings applied to a paper sheet by use of six sensors. Under this scheme, the paper sheet first passes through a first coater which applies a base coat and then travels through a stack of heating drums which dry the base coat. The sheet then travels through a second coater which applies a top coat on the base coat and then travels through a stack of heating drums which dry the top coat.

A first basis weight sensor and a moisture sensor are located upstream of the first coater. The first basis weight sensor measures the basis weight of the uncoated sheet (i.e., paper fiber and moisture). A beta ray basis weight sensor will determine the basis weight of a sheet by detecting the amount of beta rays transmitted through the sheet. An infrared moisture sensor will determine the moisture content of the sheet by detecting the amount of infrared radiation either transmitted through or reflected from the sheet in a spectral band centered about a moisture absorption peak.

A second basis weight sensor and a moisture sensor are located downstream of the first coater and upstream of the second coater. The second basis weight sensor measures the total basis weight of the sheet exiting from the first coater, including the basis weight of the paper fibers, the base coat and the moisture absorbed by the paper fibers.

The amount of paper fiber forming the sheet can be determined by subtracting the basis weight of the moisture from the basis weight of the uncoated sheet. Similarly, by subtracting the basis weight of the moisture of the base coated sheet from the basis weight of the base coated sheet, the basis weight of the base coat and paper fiber (without the moisture) can be determined. Finally, by subtracting the basis weight of paper fiber from the basis weight of the base coated sheet (without moisture), the basis weight of the base coat can be determined.

A process control computer can be used to compare the measured basis weight of the base coat at each slice with a desired value and to generate a corresponding signal to control the coating blade actuators at each slice to achieve the desired base coat profile. However, as explained below, the scheme still requires a third basis weight sensor and a moisture sensor to determine the basis weight of the top coat.

The third basis weight sensor and a moisture sensor are located downstream from both the first and the second coater. The third basis weight sensor measures the total basis weight of the sheet exiting from the second coater, including the basis weight of the paper fibers, the base coat, the top coat and the moisture content. The third moisture sensor is necessary when the heating drums are used to dry the base coat (and remove moisture from the paper) because the moisture content of the paper exiting the first coater no longer equals the moisture content of the paper exiting the second coater.

The basis weight of the top coat is calculated in the following manner. First, the measured value of the moisture content of the paper exiting the second coater is subtracted from the total basis weight of the sheet measured by the third basis weight sensor. This calculation provides the total basis weight of the top and base coat and paper fiber (without the moisture). The basis weight of the top coat is then determined by subtracting the basis weight of the paper fiber and base coat from the total basis weight of the sheet exiting the second coater.

The process control computer can then be used to compare the basis weight of the top coat at each slice across the width of the sheet with desired value(s) and to generate a corresponding signal to control coating blade actuators at each slice to achieve the desired top coat profile.

However, the above-described scheme requires six sensors which must be calibrated and kept in good working order. Moreover, the error inherent in the measurements obtained from each of these six sensors will propagate through the mathematical calculations necessary to determine the basis weight of the top and base coats.

Another scheme for measuring the amount of coating material applied to a sheet requires the irradiation of the coated sheet with very high energy x-rays which excite the atoms in the coating so that such atoms fluoresce. The fluorescing atoms emit x-rays having wavelengths unique to the elements in the coating. An x-ray can determine the amount of coating by the intensity of the fluorescence at the characteristic wavelengths.

In yet another technique, portions of the sheet are irradiated with x-rays and the intensity of the x-rays transmitted through the sheet is detected. However, x-rays are absorbed by the wood pulp fibers, moisture or mineral filler material frequently used in paper sheet. Because the transmission of x-rays is not affected by the coating material alone, sensors must be positioned before and after the coater; and the difference in transmission of the x-rays through the coated and uncoated portions of the sheet measured and related to the amount of coating material applied to the sheet. This technique requires multiple x-ray sources and sensors.

In addition, the error inherent in measurements made by each sensor may contribute to the error in the determined amount of coating.

Accordingly, the present invention provides a simpler, less expensive and more accurate sensor, system and method for measuring and controlling the amount of multiple coating layers applied to a substrate.

SUMMARY OF THE INVENTION

The present invention can be used to measure and control the amount of multiple coating layers on a substrate using measurements of radiation reflected from the substrate, or transmitted through the substrate, at least at three separate wavelength bands of the electromagnetic spectrum. The invention is primarily, but not exclusively, intended for use with an infrared radiation sensor for on-line coating measurements of a moving paper sheet. Thus, for the sake of simplicity, the invention will be described in that context. It should be understood, however, that the invention is applicable to other substrates, such as plastic, or even where the substrate may not be in sheet form.

In one embodiment, the invention includes a coating sensor which is scanned back and forth in the cross-direction across a moving sheet. The coating sensor measures the basis weight of the coatings on the base sheet along the length and width of the sheet and compensates for changes in the basis weight and moisture content of the sheet affecting the infrared transmission through or reflectance from the sheet. Therefore, the measurements remain accurate even when the basis weight or its moisture content are not uniform across the width and length of the sheet.

The coating sensor includes a source of electromagnetic radiation which transmits a beam of radiation toward the moving sheet. For the sake of simplicity, the present invention will be primarily described as using infrared radiation throughout the specification. It should be understood, however, that the invention can use other forms of electromagnetic radiation.

In any case, when a beam of electromagnetic radiation reaches the sheet it passes first through the coating and then into the base sheet. A portion of the beam (or energy) will be then transmitted through the sheet. Also, some of the energy will be reflected off the sheet. Each coating component will have its own unique absorption spectrum. For example, infrared radiation encompasses a broad range of wavelengths; however, certain wavelengths of infrared radiation are preferentially absorbed by each coating component and/or the uncoated sheet itself.

The coating sensor also includes a receiver which may located on the opposite side of the sheet from the source. In this case, the receiver measures the intensity of the portion of the beam transmitted through the sheet. Alternatively, the receiver may be located on the same side of the sheet as the source for measuring the intensity of the reflected portion of the beam. In either case, the receiver will typically include at least one beam splitter and at least three detectors with associated band pass filters. The beam splitter directs a portion of the beam toward separate detectors. A band pass filter is associated with each detector to pass that portion of the spectrum falling within the pass band.

A first band pass filter, associated with a first detector, passes wavelengths of the spectrum which are strongly absorbed by a first coating component (e.g., latex). This spectral band, the first component measure band (e.g., the latex measure band), is positioned around an absorption peak of a first coating component. Therefore, the first detector is referred to as the first component measure detector.

A second band pass filter, associated with a second detector, passes wavelengths of the spectrum which are strongly absorbed by a second coating component (e.g., clay). This band of the spectrum, the second component measure band (e.g., clay measure band), is positioned around an absorption peak of the second coating component. This band is selected so that a sheet coated with the first and second coating component absorbs more radiation than the same sheet in a first and second component reference band discussed below. The second detector is known as the second component measure detector.

A third band pass filter, associated with a third detector, passes wavelengths of the spectrum where the radiation is strongly absorbed by the base sheet, but is only weakly absorbed by (or is less sensitive to) the first and second coating components. This spectral band is referred to as the first and second component reference band and the associated detector as the first and second component reference detector. By selecting the same spectral band for the first and second component reference, the first coating component can be measured while minimizing interference from the absorption of the second coating component and vice-versa.

For reflectance sensors, the first and second component reference band is also referred to as the covering power measure band and the associated detector as the covering power measure detector. This band is more sensitive to the third coating component than the second coating component, because the third coating component has a higher covering power (i.e. backscattering power) than the second coating component. The third component backscatters radiation to the third filter and third detector which would otherwise have been absorbed by the substrate which is strongly absorbing at the third wavelength. Thus, the output signal from the third detector is primarily sensitive to absorption by the base sheet and a strong backscattering or covering third coating component (e.g., $CaCO_3$).

For transmission sensors, when the detected energy has been transmitted through the sheet from one side of the sheet to the other, the amount of absorption will depend primarily upon the cellulose fiber basis weight of the base sheet. Therefore, the ratio of the magnitude of the signal from the cover power measure detector (which is also used as the first and second reference detector) to the magnitude of the signal from the moisture and covering power reference detector indicates the paper fiber basis weight of the base sheet.

Moreover, even if the receiver and the source are located on the same side of the sheet, the output of the first and second reference detector may still be sensitive to changes in the basis weight of the base sheet. This is because the radiation is only partially reflected at the surface of the sheet. Most of the radiation penetrates into the sheet, with an increasing proportion of the total beam being reflected as it penetrates deeper into the sheet and/or encounters more sheet material. Thus, all else remaining constant, a greater basis weight sheet will reflect more energy than a lower basis weight sheet. Of course, the opposite effect would occur in a transmission coating sensor, where a greater basis weight sheet will result in less radiation being transmitted through the sheet.

When possible the first component measure band is chosen such that the average absorption by the base sheet is equivalent, or substantially equivalent, to the average absorption by the base sheet in the first and second component reference band. At the same time, the first component measure band and the first and second component reference band are chosen so that they are unequally sensitive to the first coating component. Accordingly, the ratio of the magnitude of the output signal from the first and second component reference detector divided by the magnitude of the signal from the first component measure detector indicates the amount of the first coating component.

In contrast, the second component measure band cannot be chosen such that the average absorption by the base sheet in the second component measure band is equivalent to the average absorption by the base sheet in the first and second component reference band. At the same time, the second component measure band and the first and second component reference band can be chosen so that they are unequally sensitive to the second coating component. Accordingly, the ratio of the magnitude of the output signal from the first and second component reference detector divided by the magnitude of the signal from the second component measure detector is indicative of the amount of the second coating component, but requires compensation for changes in the basis weight of the base sheet as described below.

A fourth band pass filter also may be necessary to compensate for an interfering element, which for convenience will be described hereinafter as moisture. The fourth band pass filter is associated with a fourth detector and passes wavelengths of the spectrum which are strongly absorbed by moisture in the sheet. This spectral band is called the moisture measure band and is positioned around a moisture absorption peak. The associated detector is called the moisture measure detector and provides an output signal which is used to compensate for any effect that the moisture absorption would have on the first and second component reference band.

A fifth band pass filter, associated with a fifth detector, passes a band of the spectrum which is approximately equally absorbed by an uncoated sheet, a sheet coated with the strong backscattering third coating component and the first coating component, and a sheet coated with the first and second coating components. This band of the spectrum is called the moisture and covering power reference band. The ratio of the magnitude of the output signal from the moisture reference detector to the magnitude of the signal from the moisture measure detector indicates the amount of moisture contained in the sheet. Although typical paper products contain varying moisture, a moisture-free or constant moisture sheet product may not require moisture compensation.

The fifth band pass filter is also used to pass a band of the spectrum which is used as a reference band for the basis weight or covering power measurement. As mentioned earlier, the output signal from the third detector is primarily dependent upon absorption by the base sheet and the third coating component. Thus, the ratio of the magnitude of the output signal from the covering power reference detector to the magnitude of the signal from the covering power measure detector indicates changes in the basis weight of the base sheet. This ratio can be then used to compensate for the imbalance in base sheet sensitivity between the second component measure band and the first and second component reference band.

According to the present invention, the ratio (or difference) of the output signals from the various detectors is used to determine the various select coating components and perhaps moisture. Since, as previously mentioned, radiation having wavelengths in the pass bands of both the measure and reference band pass filters are unequally sensitive to the selected components, the ratio (or difference) of the signals from the measure and reference detectors will be indicative of the amount of the coating components and moisture. Since, in the usual case, the coating components are mixed in the coating in a known fixed proportion, the amount of each coating component can be correlated with a corresponding amount of coating material.

Furthermore, because an infrared radiation source can be made Simply by electrically heating a wire, and because radiation has little or no known adverse health effects, the signal can be made as strong as necessary simply by increasing the surface area and temperature of the heated wire.

As mentioned above, signals from the coating sensor can be transmitted to a process control computer which performs the mathematical calculations provided below to provide a measurement of the amount of each coating material on the sheet. The computer compares these measurements with a desired coating amount. The computer then generates a control signal that can be used to regulate coating blade control actuators, and in turn, the amount of each coating applied to the sheet at each cross-directional position. Should conditions arise during the coating procedure which require an adjustment of the coater blade at any cross-directional position to maintain the applied coatings at the desired amount, the adjustment can be made by transmitting appropriate signals from the process control computer to one or more of the blade actuators.

Accordingly, the present invention provides a safe and highly accurate coating sensor capable of detecting multiple coating components in a system to achieve a high degree of cross-directional control over the amount and/or basis weight of the multiple coatings applied to a sheet.

BRIEF DESCRIPTION OF THE DRAWINGS

FIG. 1a is a simplified schematic perspective view of a system for monitoring and applying two coating layers to a sheet. A scanning reflectance-type infrared coating sensor according to the present invention monitors the amount of the two coatings applied to the sheet.

FIG. 1b is an enlarged view of an uncoated portion of the sheet of FIG. 1a.

FIG. 1c is an enlarged view of a base coated portion of the sheet of FIG. 1a.

FIG. 1d is an enlarged view of a top and base coated portion of the sheet of FIG. 1a.

FIG. 2 is a simplified schematic cross-sectional view of the reflectance-type infrared coating sensor of FIG. 1a.

DETAILED DESCRIPTION OF THE PREFERRED EMBODIMENTS

The following description is of the best presently contemplated mode of carrying out the invention. This description is made for the purpose of illustrating the general principles of the invention and should not be taken in a limiting sense. The scope of the invention is determined by reference to the appended claims.

Figures 1A, 1B, 1C, 1D:
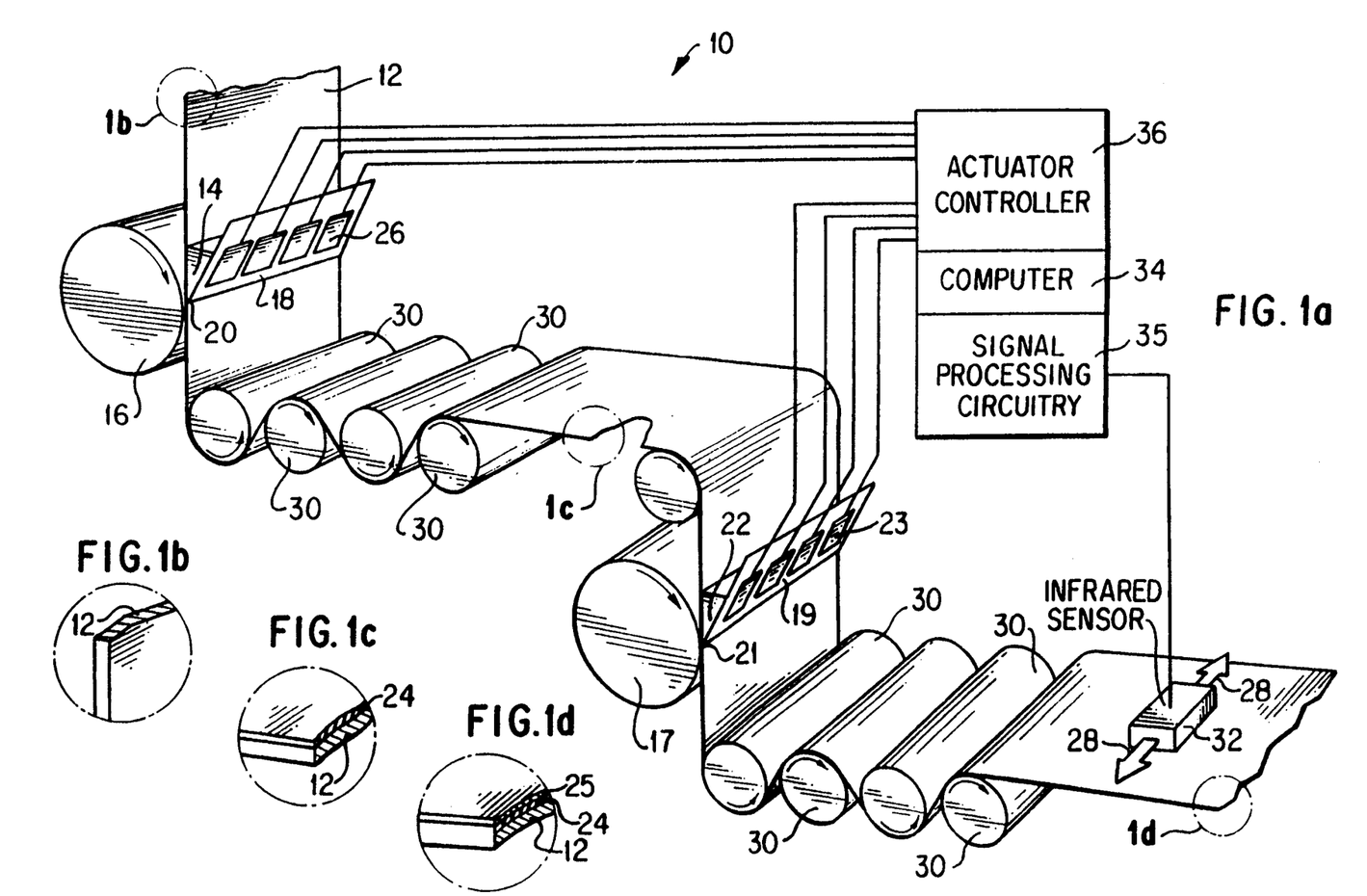

FIG. 1a illustrates a paper sheet coating system 10 for measuring and controlling the application of two coating layers. As illustrated, an uncoated paper sheet 12 (FIG. 1b) is first drawn through a supply of a base coat 14 contained between a backing roll 16 and a blade 18. As explained above, the base coat 14 may be of a paint-like substance of principally calcium carbonate ($CaCO_3$), a latex binder and possibly some clay. An exit slot 20 for sheet 12 is formed between roll 16 and the adjacent edge of blade 18, so that the thickness of a base coat 24 (FIG. 1c) on sheet 12 exiting slot 20 is determined by the distance and pressure between blade 18 and roll 16.

Actuators 26 are mounted at fixed intervals along the length of blade 18 and control the flexion of blade 18 in the vicinity of each actuator 26 such that, as actuators 26 move blade 18 toward and away from roll 16, base coat 24 on sheet 12 is made thinner and thicker, respectively. Actuators 26 are preferably spaced at 3 or 6 inch intervals. After the base coated sheet 12 exits slot 20, it passes over a number of heated drums 30 which dry the base coat 24. The dried base coated sheet 12 is then drawn through a supply of top coat 22 contained between a backing roll 17 and a blade 19. Top coat 25 (FIG. 1d) may be composed of principally clay, a latex binder and possibly some $CaCO_3$.

As with the application of base coat 24, the distance and pressure between the edge of blade 19 and roll 17 determine the thickness of top coat 25 exiting a slot 21. Actuators 23 mounted at fixed intervals along blade 19 control the flexion of blade 19 in the vicinity of each actuator 23. The actuators .23 move blade 19 toward and away from the roll 17, so that top coat 25 is made progressively thinner and thicker, respectively. Top coated sheet 12 then passes to a second set of heated drums 30 which dry the top coat 25.

The top and base coated sheet 12 then passes by a reflectance-type infrared coating weight sensor 32. Sensor 32 is driven back and forth in a scanning motion in the direction of the arrows 28 across the width of a moving top and base coated sheet 12. Accordingly, sensor 32 is able to measure the amount of infrared radiation reflected from sheet 12 at various slice positions across the width and length of sheet 12.

Signals from sensor 32 are then transmitted, via signal processing circuitry 35, to a process control computer 34, where the signals are time-wise demultiplexed so that the signals can be related to particular slice positions across the width of the sheet 12. As described below, computer 34 then performs various computations, based upon these signals, to determine the basis weight of both top coat 24 and base coat 25 at each slice. Computer 34 then compares the measured basis weights for each slice to a predetermined desired value and instructs actuator controller 36 to develop control signals which cause actuators 26 and/or 23 to flex blade 18 or 19, respectively, at each slice position to provide the desired basis weight for base coat 24 and top coat 25 for each slice. A typical goal is that basis weight of top coat 25 and base coat 24 is uniform across the width and length of sheet 12.

Figure 2:
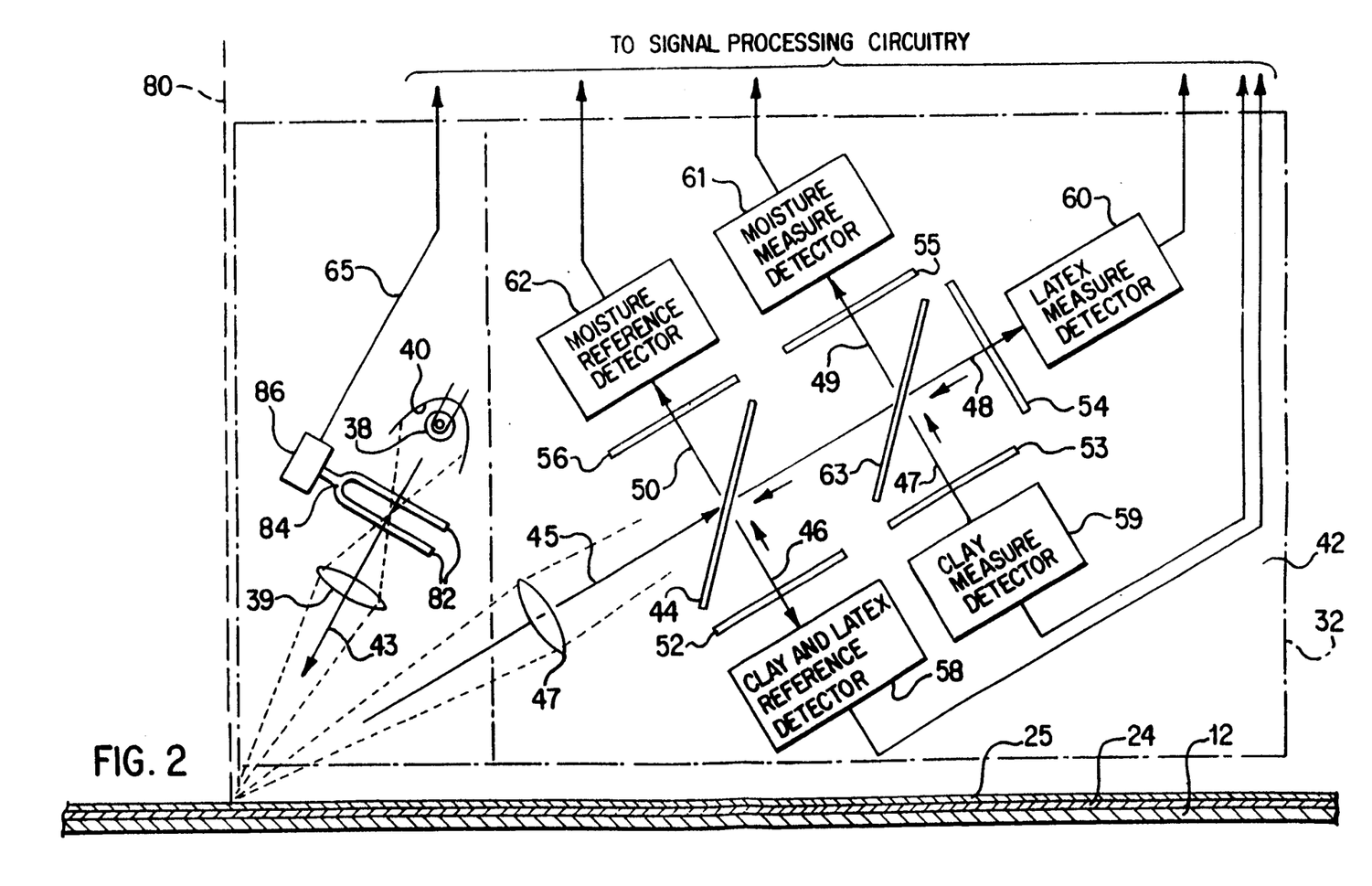

The infrared coating weight sensor 32 of FIG. 1a is illustrated in greater detail in FIG. 2. Sensor 32 is used to measure the amount of coat 24 and 25 on sheet 12 and automatically compensate for any affect resulting from changes in the basis weight and moisture content of sheet 12. Sensor 32 includes an incandescent lamp which is used as the infrared radiation source 38 and an elliptical reflector 40 which directs a beam of infrared radiation 43 from source 38 through a focusing lens 39 toward sheet 12. As illustrated in FIG. 2, the reflection-type infrared coating sensor 32, directs a beam 43 of infrared radiation toward coated sheet 12 at an angle of 10° from the normal 80 to the sheet surface.

In the preferred embodiment, sensor 32 includes a receiver 42 disposed on the same side of sheet 12 as infrared source 38 and which detects the reflected portion 45 of incident infrared beam 43. To avoid strong reflections of infrared radiation from the surface of coating 25, receiver 42 of sensor 32 is preferably constructed to detect infrared radiation reflected from the coated sheet at an angle of 20° from the same side of the normal 80 as the infrared source 38.

However, when a lightweight paper sheet is measured, a substantial portion of the infrared radiation will penetrate through sheet 12. Receiver 42 of sensor 32 may be located on the opposite side of sheet 12 from source 38 thus producing a transmission measurement. In this case, it may be desirable, but not necessary to the invention, that incident infrared beam 43 be reflected back and forth between the source and receiver sides of sensor 32 before entering a lens 47 and being subsequently detected by detectors 58, 59, 60, 61 and 62. When beam 43 is reflected repeatedly through sheet 12 in traveling from infrared source 38 to receiver 42, it has multiple opportunities to interact with the coatings 24 and 25 and sheet 12, thereby providing greater sensitivity in determining the coating basis weights.

Such multiple reflections may be achieved by positioning the receiver 42 on the opposite side of sheet 12 relative to source 38, but laterally offsetting receiver 42 from source 38, rather than directly opposing receiver 42 to source 38. Parallel reflective surfaces (not shown) on opposite sides of sheet 12 serve to repeatedly reflect beam 43 through sheet 12 and coatings 24 and 25 in traveling from source 38 to receiver 42. Various arrangements for achieving the multiple reflections through sheet 12 are described in U.S. Pat. No. 3,793,524 to Howarth, assigned to Measurex Corporation. This patent is incorporated herein by reference.

As illustrated in FIG. 2, receiver 42 includes a beam splitter 44 and a beam splitter 63 which together split the reflected infrared beam 45 into five separate beams 46, 47, 48, 49 and 50. Each of these beams is directed at a separate band pass filter 52, 53, 54, 55 and 56, positioned in the path of each of the beams immediately before detectors (typically lead sulfide detectors) 58, 59, 60, 61 and 62. Each filter 52, 53, 54, 55 and 56 is selected and aligned relative to the incoming beams 46, 47, 48, 49 and 50, so that each of these filters pass infrared radiation in a separate band of the infrared spectrum. Infrared radiation not within the pass band of the various filters 52, 53, 54, 55 and 56 is reflected by these filters back to either beam splitter 44 or 63 and thus does not reach a detector.

As a result, a single reflected beam 45 is directed from lens 47 to beam splitter 44 and 63, but the combination of beam splitters 44 and 63 and filters 52, 53, 54, 55 and 56 split beam 45 into five separate beams 46, 47, 48, 49 and 50 each detected by a different infrared detector 58, 59, 60, 61 and 62, respectively. The purpose of the various band pass filters and detectors will be further described below.

In certain situations, it may be preferred to modulate at a known frequency the amount of infrared radiation impinging upon sheet 12 from source 38. This modulation may be accomplished by any one of several devices. For example, as illustrated in FIG. 2, tines 82 of a tuning fork 84 may be disposed in the path of beam 43. The vibrating tines 82 modulate beam 43 as tines 82 move alternately into and out of the path of beam 43. Alternatively, an opaque disk (not shown) having a plurality of evenly spaced radial slots may be rotated in the path of beam 43 so that beam 43 is alternately transmitted through the slots and blocked by the opaque portions of the disk. With either device, beam 43 is modulated at a frequency. Thus, the output of each infrared detector 58, 59, 60, 61 and 62 is sinusoidally modulated at the same frequency as beam 43. Moreover, since the detector outputs are directly dependent upon the reflected portion 45 of beam 43, the phase of the detector outputs will be dependent upon the phase of the modulated beam 43. However, infrared energy originating from sheet 12, base coat 24, top coat 25, and other external sources (not shown) will also reach detectors 58, 59, 60, 61 and 62. Thus, each detector signal will include both an AC and DC component.

The output of each of detectors 58, 59, 60, 61 and 62 is transmitted to signal processing circuitry 35 (FIG. 1a). This circuitry is designed to filter out the DC component of the detector signals. The filtered AC detector signals are then passed on to a phase synchronous demodulation circuit included within the signal processing circuitry 35. The purpose of the phase synchronous demodulator is to filter out changes in the detector signals which are not caused by the varying infrared absorption of sheet 12 or of base coat 24 or of top coat 25 on sheet 12. For example, 60 HZ line noise in the detector signals is filtered out by the demodulator circuit, as explained below.

A sine wave oscillator 86 is used to drive tines 82 of a tuning fork 84 at the resonant frequency of tuning fork 84. The output of this sine wave oscillator 86, in addition to driving tuning fork 84, is also transmitted along line 65 to the signal processing circuitry 35 which converts the sine wave to a square wave having the same phase as the output signals from detectors 58, 59, 60, 61 and 62. This square wave is then fed to the phase synchronous demodulator portion of the signal processing circuitry 35 along with the filtered signals from each of detectors 58, 59, 60, 61 and 62. The signals from detectors 58, 59, 60, 61 and 62 are, of course, modulated at the same frequency as the output of sine wave oscillator 86. Hence, by demodulating the outputs from each of detectors 58, 59, 60, 61 and 62 with a square wave having the same frequency and phase and then averaging the demodulated outputs over a number of cycles changes in the detector signals which result from changes in the intensity of external infrared sources, or extraneous signals such as 60 Hz line voltage, are removed from the coating basis weight measurements. Changes in the intensity of the infrared energy reaching detectors 58, 59, 60, 61 and 62 from other external sources or 60 Hz line noise from the power supply could produce erroneous coating measurements.

The averaged amplitude of the demodulated signals from each of detectors 58, 59, 60, 61 and 62 is indicative of the amount of infrared radiation being reflected from various portions of the top and base coated sheet 12 within the pass bands of the filters 52, 53, 54, 55 and 56 associated with each detector 58, 59, 60, 61 and 62, respectively. The amplitudes of these amplitude averaged and demodulated detector signals are then measured by the signal processing circuitry 35, digitized and fed to process control computer 34. Computer 34 computes the basis weight of base coat 24 and top coat 25 using the equations and techniques described below.

Figure 3:
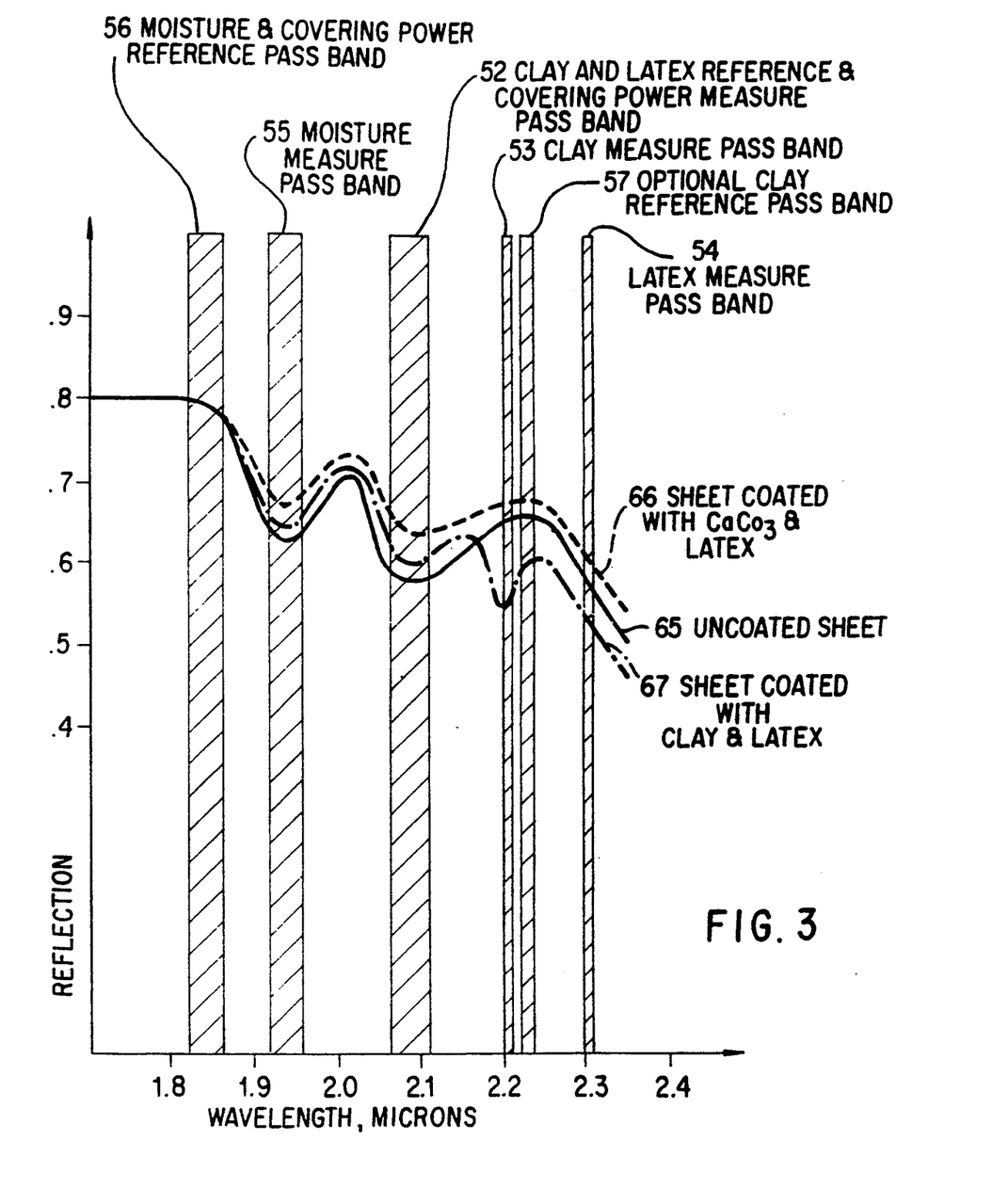
FIG. 3 illustrates an infrared backscatter reflection spectrum for a sheet coated with $CaCO_3$ and latex, a sheet coated with clay and latex, and an uncoated paper sheet.

FIG. 3 illustrates an infrared reflection spectrum 65 of an uncoated paper sheet, a spectrum 66 of a sheet coated with $CaCO_3$ and latex, and a spectrum 67 of a sheet coated with clay and latex. FIG. 3 also shows the pass band locations for the moisture reference 56, the moisture measure 55, the clay and latex reference 52, the clay measure 53, and the latex measure 54 filters associated, respectively, with the moisture reference 62, the moisture measure 61, the clay and latex reference 58, clay measure 59 and latex measure 60 detectors (FIG. 2). The clay and latex reference 52, and latex measure 54 band pass filters are chosen so that the average absorption of infrared radiation by the sheet 12 in their respective pass bands is equal, or substantially equal. In this way, the signals produced by the clay and latex reference detector 58 and latex measure detector 60 will be equal (or very nearly equal) for an uncoated sheet 12.

The preferred center wavelength for the pass bands of the moisture reference 56, moisture measure 55, clay and latex reference 52, clay measure 53 and latex measure 54 filters are about 1.84 μm, 1.94 μm, 2.09 μm, 2.21 μm and 2.30 μm, respectively. The band width for each of these filters are preferably about 0.04, 0.02, 0.04, 0.01, and 0.01 μm, respectively, but can be wider or narrower as is needed to obtain the desired signal strength and balance at the detectors.

Figure 4:
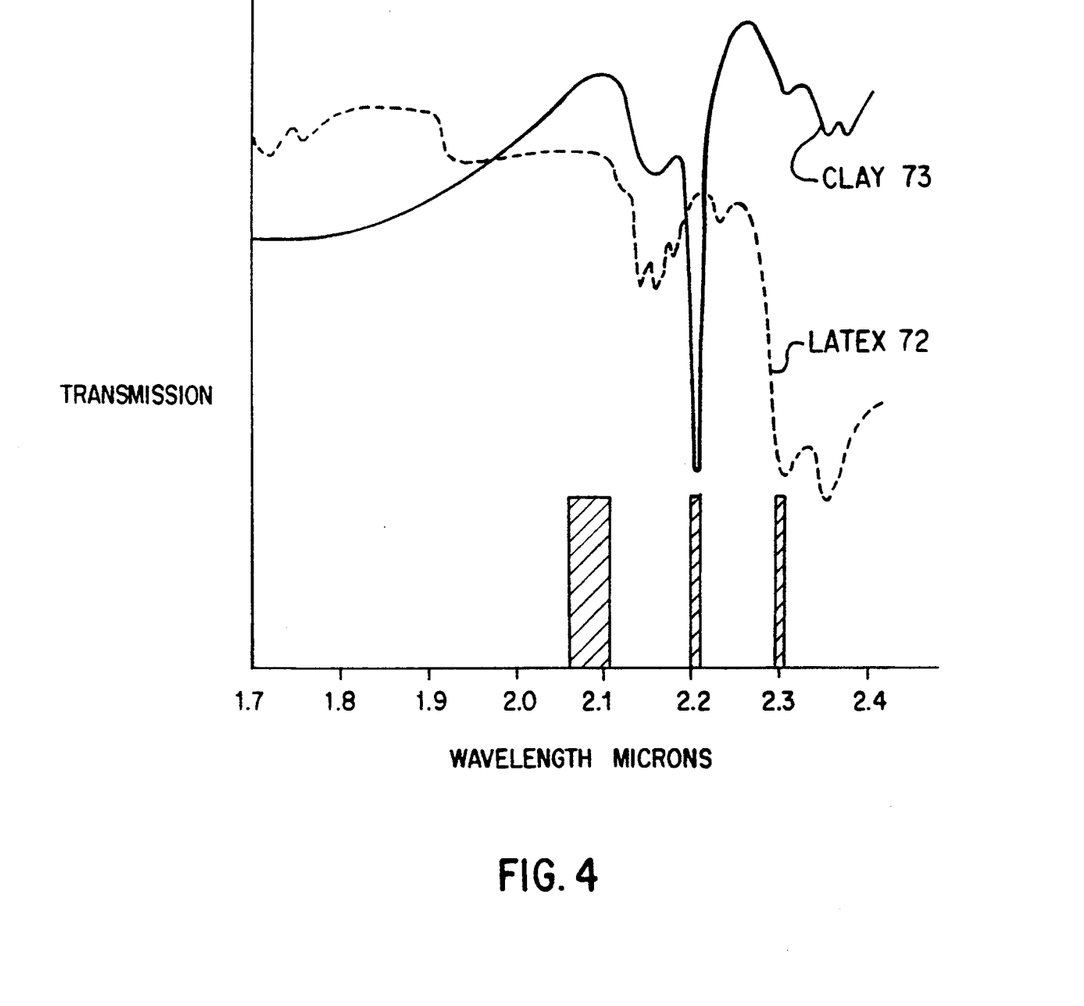
FIG. 4 illustrates an infrared transmission spectrum for a latex-type binder and for a clay component of a typical coating.

FIG. 4 illustrates an infrared transmission spectrum 72 for latex. The pass band of latex measure filter 54 falls around a strong absorption peak (or transmission minimum) at about 2.31 μm. Accordingly, with a coated sheet, the output signal from latex measure detector 60 will indicate the infrared absorption caused by the sheet 12 and the latex contained in coatings 24 and 25.

Even at its absorption peak, at typical concentrations, latex only weakly absorbs infrared radiation. Accordingly, with respect to the amount of absorption attributable to the latex component, the signal-to-noise ratio from latex measure detector 60 is so low that latex measure detector 60 by itself cannot be used to determine the amount of latex encountered by the reflected infrared beam 45. Nevertheless, because latex measure detector 60 and clay and latex reference detector 58 are equally, or substantially equally, as sensitive to the uncoated sheet 12, the ratio of the magnitude of the clay and latex reference signal divided by the magnitude of latex measure signal indicates the latex content of coatings 24 and 25. Similarly, the difference in the magnitude of the clay and latex reference and latex measure signals will also indicate the latex content of coating materials 24 and 25. Moreover, because the latex measure signal and the clay and latex reference signal are subject to the same major sources of error (e.g., changes in sheet basis weight, moisture content and dust in the optical path), the ratio or difference between the latex measure and clay and latex reference signals will provide an accurate indication of the amount of latex in the coatings 24 and 25 overlying sheet 12, even if the phase synchronized demodulation filtering technique discussed above is not used.

When setting up the coating weight sensor 32, it is important to, as much as possible, "balance" or equalize the absorption of infrared radiation by the uncoated sheet 12 in the latex measure and clay and latex reference pass bands. Known infrared band pass filters are typically made by coating a quartz substrate with a dielectric coating. The thickness of the dielectric coating determines the center of the pass band for the filter. By varying the thickness of the dielectric film, filters can be made to have a pass band at any desired band of the infrared spectrum. Alternatively, the pass band can be shifted to shorter wavelengths, at least to some extent, by tilting the filter such that the incoming infrared radiation beam strikes the filter at an angle from the surface normal. In this manner, the pass band can be fine tuned so as to balance the absorption by the sheet 12 of the radiation in the latex measure and the clay and latex reference bands.

In addition, the reflected beam 45 which reaches receiver 42 is largely reflected or backscattered off underlying paper sheet 12, which has strong scattering properties because it is made of cellulose fibers. Thus, the infrared radiation will pass through coatings 24 or 25 at least twice and the greater absorption at the latex measure band will cause an even lower output signal from latex measure detector 60 than from clay and latex reference detector 58.

FIG. 3 illustrates that spectrum 66 of the sheet coated with $CaCO_3$ and latex and spectrum 67 of the sheet coated with clay and latex have a lower magnitude at the latex measure band than at the clay and latex reference band. The magnitude of the signal from clay and latex reference detector 58 divided by the magnitude of the signal from latex measure detector 60 indicates the amount of latex in coatings 24 and 25. $Rltx = Ilref/Iltx$ is called the latex ratio.

FIG. 4 shows a strong absorption peak (or transmission minimum) in clay transmission spectrum 73 at about 2.2 μm. Accordingly, the pass band of clay measure filter 53 is chosen to fall around this absorption peak. Thus, in FIG. 3, the magnitude of spectrum 67 of the sheet coated with clay and latex is lower at the clay measure band at about 2.2 μm than at the clay and latex reference band at about 2.1 μm. This contrasts with spectrum 65 of the uncoated sheet whose magnitude at the clay measure band is greater than that at the clay and latex reference band. Thus, the ratio of the magnitude of the signal from the clay and latex reference detector 58 divided by the magnitude of the signal from clay measure detector 59 indicates the amount of clay contained in coatings 24 and 25. This ratio $Rcla = Ilref/Icla$ is called the clay ratio.

FIG. 3 also illustrates that there is a portion of the infrared radiation which is backscattered by coatings 24 and 25. This is indicated by the reflection spectra of both coated sheets 66 and 67 having a greater magnitude than spectrum 65 of the uncoated sheet at the clay and latex reference band. In addition, spectrum 66 of a sheet coated with $CaCO_3$ and latex has a larger magnitude than spectrum 67 of the sheet coated with clay and latex, because $CaCO_3$ has a higher backscattering power or "covering power" than clay.

The clay and latex reference band is selected to measure the backscattering power because at these wavelengths the paper has a strong absorption effect, while latex, clay, and CaCO₃ do not. Thus, the paper will backscatter substantially less radiation than the coatings, making the effect of the coating more significant. Because the latex, clay and CaCO₃ do not substantially absorb radiation in this band, their presence will not interfere with the backscatter measurement. The moisture reference band is also chosen as a reference for the backscatter measurement because there is relatively low absorption in this band for paper, latex, clay, and CaCO₃. Thus, the ratio of the signal from clay and latex reference detector 58 to the signal from moisture reference detector 62 indicates the amount of CaCO₃ or clay in coatings 24 and 25 and is more sensitive to CaCO₃ than to clay. This ratio Rcel=Ilref/Imref is called the cellulose or covering power ratio.

In some cases it may be difficult to set up the infrared coating sensor 32 so that the output signals from clay and latex reference detector 58 and latex measure detector 60 have the same magnitude for an uncoated sheet. Likewise, the output signals from clay and latex reference detector 58 and clay measure detector 59 do not typically have the same magnitude signal level for the uncoated paper. These values may also be affected by the basis weight of sheet 12, especially for lighter basis weight paper sheets. In these cases, the Rcel ratio is affected by the basis weight of the uncoated sheet 12 and may be used to correct for the basis weight dependence by combining the ratios Rltx and Rcel for measurement of latex, and Rcla and Rcel for measurement of clay, together with a set of appropriate weighting constants.

FIG. 3 illustrates that a strong absorption peak (or transmission minimum) due to sheet moisture is present at about 1.94 μm for all three spectra 65, 66, and 67. Thus, a moisture measure band 55 is disposed around this location. The moisture reference band 56 is placed close to the moisture measure band in order to minimize the effect of variation of scattering power with wavelength and the effect of sheet temperature. The moisture reference band could alternatively be placed at other wavelengths where there is low absorption due to moisture, paper, latex, clay and CaCO₃. For a paper sheet which has been dried to remove all moisture, the absorption in the moisture reference band and moisture measure band will be approximately equal and there should be no need to compensate for the moisture content of the sheet. However, most paper products typically contain at least some moisture. Thus, the ratio of the magnitude of the signal from the moisture reference detector 62 divided by the magnitude of the signal from the moisture measure detector 61 will indicate the amount of moisture content of the coated sheet. Because the clay and latex reference band is near a moisture absorption band, variations in moisture content will affect the amount of infrared radiation received by clay and latex reference detector 58. The above moisture-indicating ratio is thus used to compensate the coating measurements for the affects of variations in the moisture content. This Rmoi=Imref/Imoi is called the moisture ratio.

As an option, especially with a transmission sensor, we may use an additional pass band at about 2.23 μm as the clay reference. For an uncoated sheet, the absorption at this wavelength is approximately the same as that at 2.21 μm, thus the balance of the clay measure and clay reference is optimized with this choice and reduces the need for correction by Rcel.

We have thus determined four ratios which are primarily sensitive to four components of a paper sheet with two coatings: (1) Rltx, primarily sensitive to latex; (2) Rcla, primarily sensitive to clay; (3) Rcel, primarily sensitive to cellulose fiber basis weight for transmission geometries and primarily sensitive CaCO₃ or any other strongly scattering but spectrally neutral material for reflectance geometries; and (4) Rmoi, primarily sensitive to moisture and used as a correction factor. However, each of these ratios is at least partially affected by the other components. Thus, the individual components are determined by combining the various ratios defined above in a formula and using weighting coefficients determined by a multiple linear regression using actual measurements on physical samples having known coating, moisture and sheet basis weights.

One formula for making such determinations is as follows:

Coat Weight=Component/fraction

Component=A0+A1*(Rltx-1)+A2*(Rcla−1)+A3*(Rcel−1)+A4*(Rmoi−1)+A5*(Rltx−1)/(Rcel−A6).

Coat Weight=Weight per unit of a coating.
Component=Weight per unit area of a particular coating constituent, e.g., latex.
Fraction=Fraction of a coating that is a particular component. If a coating is 12% latex, then the latex fraction is 0.12.
A0 is the intercept A1 to A5 are slopes. A6 is an offset.

The last term of the formula takes into account that strongly scattering coating components (e.g., CaCO₃) backscatter some of the incident infrared radiation back to receiver 42 before it can pass through coatings 24 and 25. It should be appreciated that the strongly scattering constituents will decrease the sensitivity of the infrared sensor 32 to the latex component.

The formula can be used to determine the basis weight of a single coat on a sheet, the individual basis weight of two coatings on a sheet, and the total basis weight of a sheet with two coatings.

As previously mentioned, the calibrations constants A0, A1, A2, A3 and A5 are determined by multiple linear regression. A6 is assigned a value which is slightly greater than the value of Rcel for an uncoated sheet. A4 is determined from measurements on physical samples with several different known moisture levels. A trial value of A4 is chosen. Then the values of A0, A1, A2, A3 and A5 are determined by the linear regression. Next, the dependence of the measurements on the moisture content are calculated. This procedure is reiterated for a range of values of A4 and the value which gives the lowest moisture dependence is then selected.

A computer (not shown) may be associated with the coating weight sensor 32 and dedicated solely to performing the basis weight calculations for each slice. However, many modern paper mills are highly automated and include a process control computer 34 (FIG. 1a). In these mills, the signals produced by the infrared coating sensor 32 are preferably fed to computer 34 via signal processing circuitry 35 for computation of the amount of coating materials 24 and 25 being applied to sheet 12 at each cross-directional slice location as described above. Then, based upon these computations, computer 34 can instruct actuator controller 36 to develop signals to selectively activate coating control blade actuators 26 and 23 mounted at each slice along, respectively, blade 18 and 19 to selectively alter the amounts of coating material 24 and 25 applied to sheet 12 at each cross-directional location.

Because of economic and environmental concerns, the paper making industry is increasingly using recycled paper. The recycled paper may include carbon from ink used to print on the original sheet material, as well as latex which may have originally been applied as a sheet coating but which during the recycling process has been incorporated into the recycled base sheet material.

An advantage of the present invention is that the carbon associated with ink absorbs infrared radiation with equal efficiency across the entire band interest of the infrared spectra. Accordingly, during operation of the present invention, there is no need to rebalance clay and latex reference detector 58 and latex measure detector 60 when recycled paper including carbon-based ink is used in the manufacturing process.

On the other hand, it may happen that latex is also incorporated into sheet 12. In this situation, a secondary infrared sensor (not shown), similar or identical to the primary infrared sensor 32 described above, is positioned at a location in the paper coating process prior to the application of the coating material 24 to the sheet. This secondary sensor is disposed adjacent to the uncoated base sheet and used to measure the amount of latex in the base sheet in exactly the same manner as described above for the primary sensor. In this situation, computer 34 receives signals from the secondary sensor, computes the amount of latex incorporated into the base sheet, and subtracts this latex measurement from the latex measurement resulting from the signals supplied to the computer 34 by the primary coating sensor 32. The difference resulting from this subtraction is indicative of the amount of latex in the coating material applied to the recycled base paper sheet. A similar technique can be used to compensate for other constituents in the base sheet which are also in the coating materials. Coating control is then conducted in a manner identical to that previously described.

Finally, as previously mentioned, latex is usually used as a binder in the coating material which may include a number of other chemical components such as dies, fillers, etc. These components are mixed in precise known proportions with the latex component of the coating. Accordingly, by determining the amount of the latex component overlying a sheet, a computer can also determine the total amount of the entire coating mixture on the sheet from the known proportions of the other components of the coating material to the latex component.

One embodiment of the present invention has been described in detail above. Nevertheless, it is understood that one may make various modifications without departing from the spirit and scope of the invention. For example, where the coating material includes other coating components having different absorption peaks, the principles of the present invention can still be used as described above to measure and control the amount of coating applied to such paper based upon measurements of the latex in the encapsulating material. Moreover, the present invention is not limited to use with paper, nor to latex-based coating materials, nor infrared radiation. The present invention is also applicable to other substrate materials and to other coating materials as well as to bands of the electromagnetic spectrum other than the infrared band. Furthermore, although it is generally desirable to choose a reference wavelength band such that the radiation within the reference band is only weakly absorbed by the selected coating components, it is sufficient for the operation of a device embodying the invention that the radiation in the reference and measure wavelength band simply be unequally sensitive to absorption by the selected coating components. Thus, the scope of the invention is not limited to the embodiment described in detail herein.

We claim:

1. A coating sensor for sensing the amount of at least one layer of coating material on a substrate, wherein the at least one layer of coating material includes at least two components, the sensor comprising:
    a radiation source disposed to direct a beam of radiation into the coated substrate; and
    a radiation receiver disposed to detect at least a portion of the beam emerging from the coated substrate, the receiver being configured to detect the amount of radiation in first, second and third separate wavelength bands of the radiation spectrum and to produce first, second and third signals therefrom, respectively, indicating the amount of detected radiation in the first, second and third bands, wherein the first band is selected for radiation which is sensitive to the amount of a first component, the second band is selected for radiation which is sensitive to the amount of a second component and the third band is selected for radiation which is sensitive to the amount of the substrate.

2. A coating sensor as in claim 1, wherein the first band and third band are unequally sensitive tot he amount of the first component, the second and third band are unequally sensitive to the amount of the second component.

3. A coating sensor as in claim 2, wherein the first band is more sensitive than the third band to the amount of the first component.

4. A coating sensor as in claim 2, wherein the second band is more sensitive than the third band to the amount of the second component.

5. A coating sensor as in claim 2, wherein the first band is more sensitive than the third band to the first component and the second band is more sensitive than the third band to the amount of the second component.

6. A coating sensor as in claim 1, wherein the first and third band are approximately equal or equally sensitive to the amount of the substrate.

7. A coating sensor as in claim 1, wherein the third band is selected to be also sensitive to the amount of a third component.

8. A coating sensor as in claim 7, wherein the third component has higher covering power than the second component and the third band is more sensitive to the amount of the third component than to the amount of the second component.

9. A coating sensor as in claim 7, wherein the first component is latex and the first band is centered around approximately 2.30 $\mu$m, the second component is clay and the second band is centered around approximately 2.21 $\mu$m, and the substrate is paper and the third component is $CaCO_3$ and the third band is centered around approximately 2.09 $\mu$m.

10. A coating sensor as in claim 1, wherein the radiation is infrared radiation.

11. A coating sensor as in claim 1, wherein the receiver is further configured to detect the amount of radiation in a fourth and fifth band and to produce a fourth and fifth signals therefrom, respectively, indicating the amount of detected radiation in the fourth and fifth bands, wherein the fourth band is selected for radiation which is more sensitive than the fifth band to the amount of an interfering component associated with the substrate.

12. A coating sensor as in claim 11, wherein the substrate is paper and the fifth band is centered around approximately 1.84 $\mu$m, the interfering component is water and the fourth band is centered around approximately 1.94 $\mu$m.

13. A coating sensor as in claim 1, wherein the receiver is configured to further detect the amount of radiation in a fourth band and to produce a fourth signal indicating the amount of detected radiation in the fourth band, wherein the fourth band is selected for radiation which is substantially equally or equally sensitive to the substrate, tot he substrate coated with the first component and a third component, and to the substrate coated with the first ad second components.

14. A coating sensor as in claim 13, wherein the fourth band is centered around approximately 1.84 $\mu$m.

15. A coating sensor as in claim 1, further comprising computing means operatively coupled to the receiver for computing the amount of the first component from at least the first and third signals.

16. A coating sensor as in claim 1, further comprising computing means operatively coupled to the receiver for computing the amount of the second component from at least the second and third signals.

17. A coating sensor as in claim 11, further comprising computing means operatively coupled to the receiver for computing the amount of the substrate from at least the third and fifth signals.

18. A coating sensor as in claim 11, further comprising computing means operatively coupled to the receiver for computing the amount of the third component from at least the third and fifth signals.

19. A coating sensor as in claim 11, further comprising computing means operatively coupled to the receiver for computing the amount of the interfering component from at least the fourth and fifth signals.

20. A coating sensor as in claim 11, further comprising:
   a scanning mechanism, having the receiver attached thereto, for scanning the receiver back and forth along a line; and
   a computer operatively coupled to the receiver for receiving the first, second, third, fourth and fifth signals and determining the amount of at least one component on the substrate at various positions of the substrate traversed by the scanning sensor from the first, second, third, fourth and fifth signals.

21. A coating system for applying a controlled amount of at least two coating layers to a moving substrate with each of the coating layers using a coating material that includes at least two components, the system comprising:
   a substrate coating apparatus for applying two coating layers to the substrate, the coating apparatus including a first metering element for regulating the amount of the first coating layer and a second metering element for regulating the amount of the second coating layer material which remain on the substrate after the substrate passes by the first and second metering element, respectively;
   a first coating sensor disposed adjacent to the coated substrate and including a first radiation source disposed to direct a first beam of radiation into the substrate and a first radiation receiver positioned to detect at least a portion of the first beam emerging from the coated substrate, the receiver being configured to detect the amount of radiation in first, second, third, fourth and fifth wavelength bands of the radiation spectrum and to produce first, second, third, fourth and fifth signals therefrom, respectively, indicating the amount of detected radiation in the first, second, third, fourth and fifth bands, wherein the first band is selected for radion which is sensitive to the amount of a first component, the second band is selected for radion which is sensitive to the amount of a second component, the third band is selected for radiation which is sensitive to the amount of the substrate and to the amount of a third component, the fourth band is selected for radiation which is sensitive to the amount of an interfering component associated with the substrate, the fifth band is selected for radiation which is substantially equally or equally sensitive to the substrate, to the substrate coated with the first and third components, and to the substrate coated with the first and second components, the first and third band being unequally sensitive to the amount of the first components, the second and third band being unequally sensitive to the amount of the second component, the third and fifth band being unequally sensitive to the amount of the third component and the fourth and fifth band being unequally sensitive to the amount of the interfering component;
   a computer operatively coupled to the first receiver for computing the amount of the first and second coating layer on the substrate from the first, second, third, fourth and fifth signals, the computer producing a first and second control signal, respectively, indicating the computed amount of the first and second coating layers;
   a first actuator, operatively coupled to the computer and to the first metering element, for adjusting the metering element in response to the first control signal to regulate the amount of the first coating layer of the substrate; and
   a second actuator, operatively coupled to the computer and to the second metering element, for adjusting the metering element in response to the second control signal to regulate the amount of the second coating layer on the substrate.

22. A coating system as in claim 21, wherein the radiation is infrared radiation.

23. A coating system as in claim 22, wherein the first component is latex and the first band is centered around approximately 2.30 $\mu$m, the second component is clay and the second band is centered around approximately 2.21 $\mu$m, the substrate is paper and the third component is $CaCO_3$ and the third band is centered around approximately 2.09 $\mu$m, the interfering component is water and the fourth band is centered around approximately 1.94 $\mu$m and the fifth band is the third component and moisture reference band and is centered around approximately 1.84 $\mu$m.

24. A coating system as in claim 23, further comprising a scanning mechanism, having the first sensor attached thereto, for scanning the first sensor back and forth along a line, and wherein the computer is programmed to determine the amount of the first and second coating layer on the substrate at various cross-directional position of the substrate traversed by the scanning first sensor from the first, second, third, fourth and fifth signals.

* * * * *